US005882668A

United States Patent [19]
Garnaat et al.

[11] Patent Number: 5,882,668
[45] Date of Patent: *Mar. 16, 1999

[54] MAIZE PROTEIN FOR INSECT CONTROL

[75] Inventors: Carl W. Garnaat, Ankeny; Terry EuClaire Meyer, Urbandale, both of Iowa

[73] Assignee: Pioneer Hi-Bred International, Inc., Des Moines, Iowa

[ * ] Notice: This patent issued on a continued prosecution application filed under 37 CFR 1.53(d), and is subject to the twenty year patent term provisions of 35 U.S.C. 154(a)(2).

[21] Appl. No.: 756,855

[22] Filed: Nov. 26, 1996

Related U.S. Application Data

[62] Division of Ser. No. 449,986, May 25, 1995, Pat. No. 5,824,864.

[51] Int. Cl.⁶ .................................................. A01N 25/00
[52] U.S. Cl. .............................. 424/405; 514/2; 530/324; 530/350
[58] Field of Search .................................. 530/350, 324; 514/62, 2; 424/405

[56] References Cited

U.S. PATENT DOCUMENTS

| | | |
|---|---|---|
| 4,522,803 | 6/1985 | Lenk et al. . |
| 4,588,578 | 5/1986 | Fountain et al. . |
| 5,034,322 | 7/1991 | Rogers et al. . |
| 5,071,654 | 12/1991 | English . |
| 5,157,207 | 10/1992 | Carlson et al. . |
| 5,234,834 | 8/1993 | Fischer et al. . |

FOREIGN PATENT DOCUMENTS

| | | |
|---|---|---|
| 2090552 | 8/1994 | Canada . |
| WO 9322441 | 11/1993 | WIPO . |
| WO 9421805 | 9/1994 | WIPO . |
| WO 9501098 | 1/1995 | WIPO . |

OTHER PUBLICATIONS

Maniatis et al., "Molecular Cloning; A Laboratory Manual" Cold Spring Harbor Laboratories, Cold Spring Manual N.Y., 1982.

*Macromolecular Sequencing & Synthesis* Alan R. Ziss' NY NY Chapter 12: Current Methods in Sequence Comparison & Analysis pp. 127–149, 1988.

Andrews et al. (1988) Characterization of the lipid acyl hydrolase activity of the major potato (*Solanum tuberosum*) tuber protein, patatin, by cloning and abundant expression in a baculovirus vector, *Biochem. J.*, 252:199–206.

Berry–Lowe, et al. (1982) The nucleotide sequence, expression, and evolution of one member of a multigene family encoding the small subunit of ribulose–1,5–bisphosphate carboxylase in soybean, *Journal of Molecular and Applied Genetics*, vol. 1, No. 6, pp.–483–498.

Bogusz, et al. (1990) Nonlegume hemoglobin genes retain organ–specific expression in heterologous transgenic plants, *The Plant Cell*, vol. 2, pp. 633–641.

Boulter et al. (1989) Use of cowpea trypsin inhibitor (CpTI) to protect plants against insect predation, *Biotech. Adv.*, vol. 7, pp. 489–497.

Broadway et al. (1986) Plant proteinase inhibitors: Mechanism of action and effect on the growth and digestive physiology of larval *Heliothis zea* and *Spodoptera exiqua, J. Insect Physiol.*, vol. 32, No. 10, pp. 827–833.

Cashmore, A.R. (1983) Nuclear Genes Encoding the Small Subunit of Ribulose–1,5–Bisphosphate Carboxylase, *Genetic Engineering of Plants, an Agricultural Perspective*, pp. 29–38.

Coruzzi, et al. (1983) Nucleotide Sequences of Two Pea cDNA Clones Encoding the Small Subunit of Ribulose 1,5–Bisphosphate Carboxylase and the Major Chlorophyll α/β–binding Thylakoid Polypeptide, *The Journal of Biological Chemistry*, vol. 258, pp. 1399–1402.

Czapla et al. (1990) Effect of Plant Lectins on the Larval Development of European Corn Borer (Lepidoptera: Pyralidae) and Southern Corn Rootworm (*Coleoptera: Chrysomelidae*) *Journal of Economic Entomology*, vol. 83, No. 6, pp.–2480–2485.

Dunsmuir et al. (1983) The Major Chlorophyll α/β Binding Protein of Petunia is Composed of Several Polypeptides Encoded by a Number of Distinct Nuclear Genes, *Journal of Molecular and Applied Genetics*, 2:285–300.

Galliard, T. (1971) The enzymic deacylatin of phospholipids and galactolipids in plants, *Biochem. J.*, 121:379–390.

Ganal et al. (1991) Genetic and Physical Mapping of the Patatin Genes in Potato and Tomato, *Mol. Gen. Genet.*, 225:501–509.

Gatehouse et al. (1986) The effects of α–Amylase Inhibitors on Insect Storage Pests: Inhibition of α–Amylase in vitro and Effects on Development in vivo. *J. Sci. Food Agric.*, 37:727–734.

Hirel et al. (1992) Forcing expression of a soybean root glutamine synthetase gene in tobacco leaves induces a native gene encoding cytosolic enzyme, *Plant Molecular Biology*, 20:207–218.

Hofgen et al. (1990) Biochemical and Genetic Analysis of Different Patatin Isoforms Expressed in Various Organs of Potato (*Solanum Tuberosum*), *Plant Science*, 66:221–230.

Ishimoto et al. (1989) Growth inhibitory effects of an α–amylase inhibitor from the kidney bean, *Phaseolus vulgaris* (L.) on three species of bruchids (coleoptera: bruchidae), *App. Ent. Zool*24:(3): 281–286.

Keller et al. (1991) Vascular–Specific Expression of the Bean GRP 1.8 Gene is Negatively Regulated, *The Plant Cell*, vol. 3, pp.–1051–1061.

(List continued on next page.)

*Primary Examiner*—Cecilia J. Tsang
*Assistant Examiner*—Patrick R. Delaney

[57] ABSTRACT

Nucleotide sequences encoding a maize 5C9 polypeptide, the 5C9 polypeptide and structural and functional equivalents, and methods for controlling insect infestation in plants are provided.

7 Claims, 4 Drawing Sheets

OTHER PUBLICATIONS

Leach et al. (1991) Promoter analysis of the highly expressed rolC and rolD root–inducing genes of *Agrobacterium rhizogenes*: enhancer and tissue–specific DNA determinants are dissociated, *Plant Science*, vol. 79, pp. 69–76.

Miao et al. (1991) Ammonia–Regulated Expression of a Soybean gene Encoding Cytosolic Glutamine Synthetase in Transgenic Lotus Corniculatus, *The Plant Cell*, vol. 3, pp. 11–22.

Mignery et al. (1984) Isolation and Sequence analysis of cDNAs for the Major Potato Tuber Protein, Patatin, *Nucleic Acids Research*, vol. 12, No. 21, pp. 7987–8001.

Mignery et al. (1988) Molecular characterization of the patatin multigene family of potato, *Gene*, 62:27–44.

Murdock et al. (1990) Biological effects of plant lectins on the cowpea weevil, Phytochemistry, vol. 29, No. 1, pp. 85–89.

Racusen, David (1986) Esterace specificity of patatin from two potato cultivars[1], *Can. J. Bot.*, vol. 64, pp.–2104–2106.

Racusen, David (1984) Lipid acyl hydrolase of patatin[1], *Can. J. Bot.*, vol. 62, pp. 1640–1644.

Rosahl et al. (1987) Expression of a Tuber–Specific Storage Protein in Transgenic Tobacco Plants: Demonstation of an Esterase Activity, *The EMBO Journal*, vol. 6, No. 5, pp. 1155–1159.

Sanger et al. (1990) Characteristics of a strong promoter from figwort mosaic virus: comparison with the analogous 35S promoter from cauliflower mosaic virus and the regulated mannopine synthase promoter, *Plant Molecular Biology*, 14:433–443.

Shukle et al. (1983) Lipoxygenase, Trypsin Inhibitor, and Lectin from Soybeans: Effects on Larval Growth of *Manduca sexta* (Lepidoptera: Sphingidae)[1], *Environmental Entomology*, vol. 12, No. 3, pp. 787–791.

Stiekema et al. (1988) Molecular Cloning and Analysis of Four Potato Tuber mRMAs, *Plant Molecular Biology*, 11:255–269.

Teeri et al. (1989) Gene fusions to lacZ reveal new expression patterns of chimeric genes in transgenic plants, *The EMBO Journal*, vol. 8, No. 2, pp. 343–350.

Vancanneyt et al. (1989) Expression of a Patatin–like Protein in the Anthers of Potato and Sweet Pepper Flowers, *The Plant Cell*, vol. 1, 553–540.

Weiss et al. (1994) Isolation of cDNAs encoding guanine nucleotide–binding protein β–subunit homologues from maize (ZGB1) and Arabidopsis (AGB1), *Proc. Natl. Acad. Sci. USA*, vol. 91, pp. 9554–9558.

Saczynska, Violeeta, et al., (1994) Effects of pH and detergents on galactolipase activity in chloroplasts of chilling–sensitive and chilling resistant plants, *ACTA Physiologiae Planatarum* vol. 16, No. 4, pp. 317–328.

|      |            |            |            |            |            |
|-----:|------------|------------|------------|------------|------------|
|    1 | GAATTCGGCA | CGAGCACACA | CAAGCGAGGA | GCACTACCTG | TTGGTTGGAT |
|   51 | TCTCTTCAGT | CTAGCTACTC | GATCGGTCCC | TTGTCCACAG | TTAAGTTTCA |
|  101 | GACACATGGG | GAGCATTGGC | AGAGGCACGG | CCAACTGCGC | CACCGTGCCG |
|  151 | CAGCCGCCGC | CGTCGACAGG | GAAGCTCATC | ACGATCCTGA | GCATCGATGG |
|  201 | CGGCGGCATC | CGCGGCCTTA | TCCCGGCGAC | CATCATTGCG | TACCTCGAGG |
|  251 | CCAAGCTCCA | GGAGCTGGAC | GGCCCGGACG | CTCGGATCGC | CGACTACTTC |
|  301 | GATGTGATTG | CCGGGACGAG | CACCGGCGCC | CTGCTCGCGT | CGATGCTGGC |
|  351 | GGCGCCGGAC | GAGAACAACC | GGCCGCTGTT | CGCCGCCAAG | GACCTCACCA |
|  401 | CGTTCTACCT | CGAGAACGGC | CCAAAGATCT | CCCACAGAA  | AAAGGCTGGG |
|  451 | TTGCTGACGC | CGCTGAGGAA | CCTGCTGGGC | CTGGTGCGGG | GCCCCAAGTA |
|  501 | CGACGGCGTG | TTCCTGCACG | ACAAGATCAA | GAGCCTGACG | CACGACGTCA |
|  551 | GGGTGGCGGA | CACGGTGACC | AACGTCATCG | TGCCGGCGTT | CGACGTCAAG |
|  601 | TACCTGCAGC | CCATCATCTT | CTCGACGTAC | GAGGCCAAGA | CCGACACCCT |
|  651 | CAAGAACGCG | CACCTCTCCG | ACATCTGCAT | CAGCACGTCG | GCGGCGCCCA |
|  701 | CCTACTTCCC | GGCGCACTTC | TTCAAGACCG | AGGCCACCGA | CGGCCGGCCC |
|  751 | CCCCGCGAGT | ACCACCTCGT | GGACGGCGGC | GTCGCGGCCA | ACAACCCCAC |
|  801 | CATGGTCGCC | ATGTCCATGC | TCACCAAGGA | GGTGCACCGC | CGCAACCCCA |
|  851 | ACTTCAACGC | CGGCAGCCCC | ACCGAGTACA | CCAACTACCT | CATCATCTCC |
|  901 | GTCGGCACCG | GGTCGGCAAA | GCAGGCGGAG | AAGTACACCG | CGGAGCAGTG |
|  951 | CGCGAAGTGG | GGCCTCATCC | AGTGGCTCTA | CAACGGCGGC | TTCACGCCGA |
| 1001 | TCATCGACAT | CTTCTCGCAT | GCCAGTTCCG | ACATGGTTGA | CATCCATGCG |
| 1051 | TCGATCCTCT | TTCAGGCCCT | GCACTGCGAG | AAGAAGTACC | TTCGCATCCA |
| 1101 | GGATGATACT | TTGACTGGGA | ACGCATCGTC | CGTGGACATC | GCCACCAAGG |
| 1151 | AGAACATGGA | GTCTCTGATA | TCGATCGGCC | AGGAGCTGCT | CAAGAAGCCA |
| 1201 | GTGGCGAGAG | TGAACATCGA | CACAGGGGTG | TACGAGTCCT | GCGACGGTGA |
| 1251 | GGGCACAAAT | GCACAGTCGC | TAGCTGACTT | CGCCAAGCAA | CTCTCTGACG |
| 1301 | AGCGCAAGCT | ACGCAAGAGC | AATCTCAACT | CCAACTAATA | AATACCTCTC |
| 1351 | TCAGTCACAG | CATGTGCTCT | TTCTGCAGAT | TCACCGTTTC | TTATTTTTAA |
| 1401 | TTTCAATTTC | AATTCAGTGT | ATGTGCGTGT | GTGTGTGACT | GTACTGTGTG |
| 1451 | TACCAATAAA | CATTTAAGTT | CAATCATTTG | CTTGTCTATG | ATCAAAAGAA |
| 1501 | CCATTTCCTT | CTGAAAAAAA | AACGGCACGA | G          |            |

*FIG.1*

```
  1  MGSIGRGTAN  CATVPQPPPS  TGKLITILSI  DGGGIRGLIP  ATIIAYLEAK
 51  LQELDGPDAR  IADYFDVIAG  TSTGALLASM  LAAPDENNRP  LFAAKDLTTF
101  YLENGPKIFP  QKKAGLLTPL  RNLLGLVRGP  KYDGVFLHDK  IKSLTHDVRV
151  ADTVTNVIVP  AFDVKYLQPI  IFSTYEAKTD  TLKNAHLSDI  CISTSAAPTY
201  FPAHFFKTEA  TDGRPPREYH  LVDGGVAANN  PTMVAMSMLT  KEVHRRNPNF
251  NAGSPTEYTN  YLIISVGTGS  AKQAEKYTAE  QCAKWGLIQW  LYNGGFTPII
301  DIFSHASSDM  VDIHASILFQ  ALHCEKKYLR  IQDDTLTGNA  SSVDIATKEN
351  MESLISIGQE  LLKKPVARVN  IDTGVYESCD  GEGTNAQSLA  DFAKQLSDER
401  KLRKSNLNSN
```

MAIZE PROTEIN FOR INSECT CONTROL

This is a divisional application of prior application Ser. No. 08/449,986, filed May 25, 1995 now U.S. Pat. No. 5,824,864.

FIELD OF THE INVENTION

The present invention relates to the field of plant molecular biology. More specifically, the invention relates to isolated maize nucleotide sequences encoding an insecticidal polypeptide, and methods for control of insect infestation in plants.

BACKGROUND

The use of natural products, including proteins, is a well known method of controlling many insect pests. For example, endotoxins of *Bacillus thuringiensis* (*B.t.*) are used to control both lepidopteran and coleopteran insect pests. Genes producing these endotoxins have been introduced into and expressed by various plants, including cotton, tobacco, tomato, and maize. There are, however, several economically important insect pests that are not susceptible to *B.t.* endotoxins, including the boll weevil, *Anthonomus grandis*, and corn rootworm (CRW), *Diabrotica* spp. In addition, having other, different gene products for control of insects which are susceptible to *B.t.* endotoxins is critical for resistance management.

Several other known insecticidal proteins are found in plants. These include lectins, amylase inhibitors, and protease inhibitors, which can affect insect growth and development when ingested at high levels. See, e.g., Boulter et al., 1989; Broadway and Duffey, 1986, Czapla and Lang, 1990; Gatehouse et al., 1986, Heusing et al., 1991; Ishimoto and K. Kitamura, 1989, Murdock et al., 1990; Shuckle and Murdock, 1993. However, these proteins apparently do not provide the acute mortality afforded by B.t proteins.

Patatins are a family of proteins found in potato (see Gaillaird, 1971; Racusen, 1984; Andrews et al., 1988) and other plants, particularly in solanaceous plants (Ganal et al., 1991; Vancanneyt et al., 1989). In potato the patatins are found primarily in tubers, but also at much lower levels in other plant organs (Hofgen and Willmitzer, 1990). Genes that encode patatins have been isolated. See, e.g., Mignery et al., 1984; Mignery et al., 1988; Stiekema et al., 1988. Roshal et al., 1987, transferred a patatin gene to tobacco and expressed patatin in transgenic tobacco plants.

Although the benefits of expression of heterologous genes in transgenic plants cannot be minimized, there are additional benefits to be gained from discovering native or autologous genes, the copy number of which and/or the expression of which can be increased. In addition, even when a heterologous gene is inserted into and expressed in transgenic plants, if that gene is isolated from a somewhat more closely related species, its expression level may be higher than in instances where genes from unrelated species are used, and its expression product may be more effective. Therefore, an effective insect control protein from an agronomic crop species is highly desirable.

SUMMARY

It is therefore an object of the present invention to provide isolated maize nucleotide sequences showing some sequence similarity to, but that are not substantially homologous to, genes encoding patatins and the proteins encoded thereby. It is a further object of this invention to provide expression cassettes, useful in the transformation of plant cells, that contain the isolated maize nucleotide sequences encoding the proteins of the invention.

It is also an object of the present invention to provide methods for controlling insect infestation of plants. In one aspect of the invention this comprises providing an effective amount of the insecticidal polypeptide 5C9 for ingestion by the insect. This may be accomplished by providing an insecticidally effective amount of the protein into the environment of the insects, for example by spraying or other application techniques, or by providing plant-colonizing microorganisms that have been transformed to express the isolated nucleotide sequences of the invention and which are introduced to the plant, express such gene, and provide an insecticidally effective amount of the protein.

Alternatively, the method may be effected by genetically transforming the plant to express either additional, insecticidally effective levels of the native insecticidal protein (in instances where the transformed plant is a maize plant), or to express insecticidally effective levels of the heterologous insecticidal protein (in instances where the transformed plant is other than a maize plant). The method of the invention further envisions specifically increasing the expression of the active 5C9 protein in maize by increasing its copy number and/or replacing its promoter with an over-expressing promoter, such as a constitutive or a tissue specific promoter.

In addition, the present invention also provides the method of controlling insect infestation in plants by imparting insect resistance to plants of taxons susceptible to infestation. Fertile, insect resistant plants from sexually compatible taxa that have been transformed with DNA encoding the 5C9 polypeptide of the invention, are selected and sexually crossed with a plant from the infestation-susceptible taxon. Reproductive material is recovered from the progeny of the cross, and insect resistant plants are grown up from that reproductive material. To impart resistance in taxa consisting of substantially homozygous plants the method further comprises repetitive backcrossing of the insect resistant progeny with substantially homozygous, infestation-susceptible plants from the taxon, and selecting for expression of insect resistance along with any other desired characteristics of the susceptible taxon from among the progeny of the backcross, until the desired percentage of the characteristics of the susceptible taxon are present in the progeny, along with insect resistance.

Alternatively, the invention also envisions the screening of maize plants for mutants having altered expression patterns of 5C9 such that protection against insects or other plant pathogens is increased in tissues in which 5C9 is not normally expressed, or in tissues in which expression does not occur at such effective levels.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from the following detailed description.

BRIEF DESCRIPTION OF THE DRAWINGS

FIG. 1 is the sequence (SEQ ID NO:1) of the isolated maize cDNA sequence encoding the 5C9 polypeptide.

DETAILED DESCRIPTION

Figure 2:
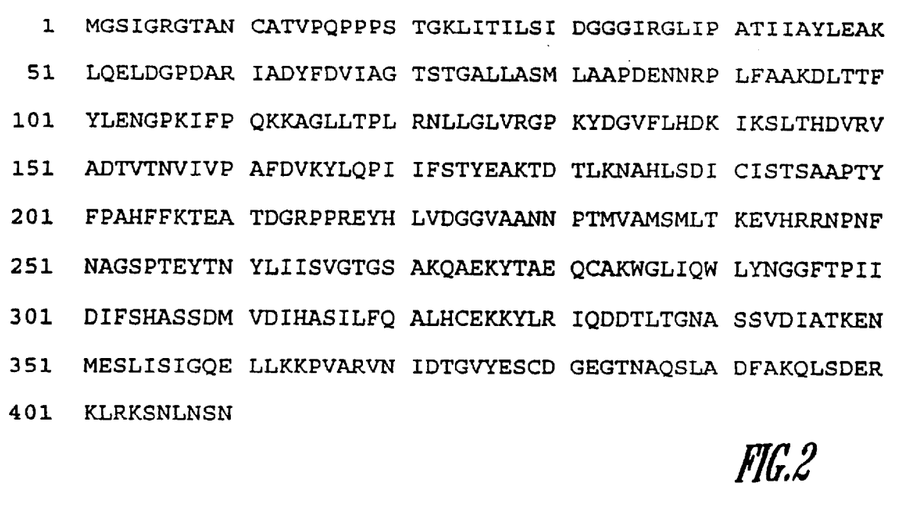
FIG. 2 is the deduced amino acid sequence (SEQ ID NO:2) of the 5C9 polypeptide.
Figure 3:
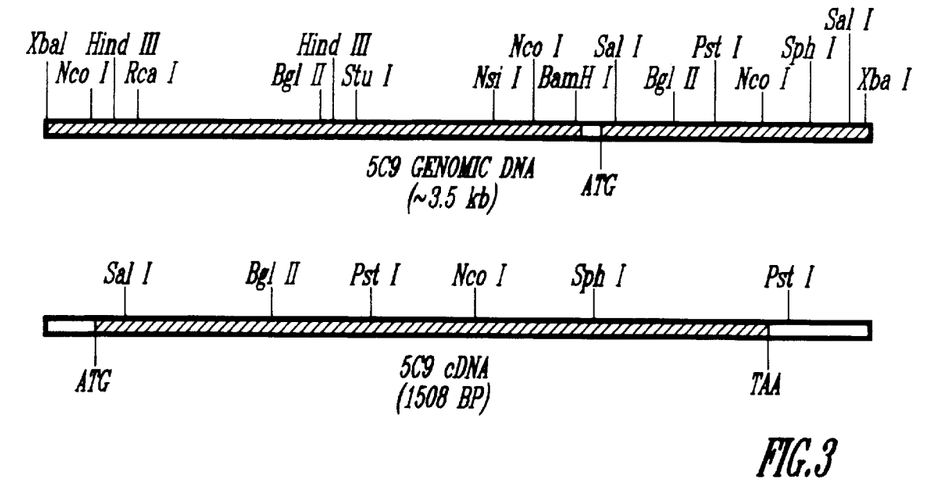
FIG. 3 is a schematic of 5C9 genomic and cDNA inserts.
Figure 4:
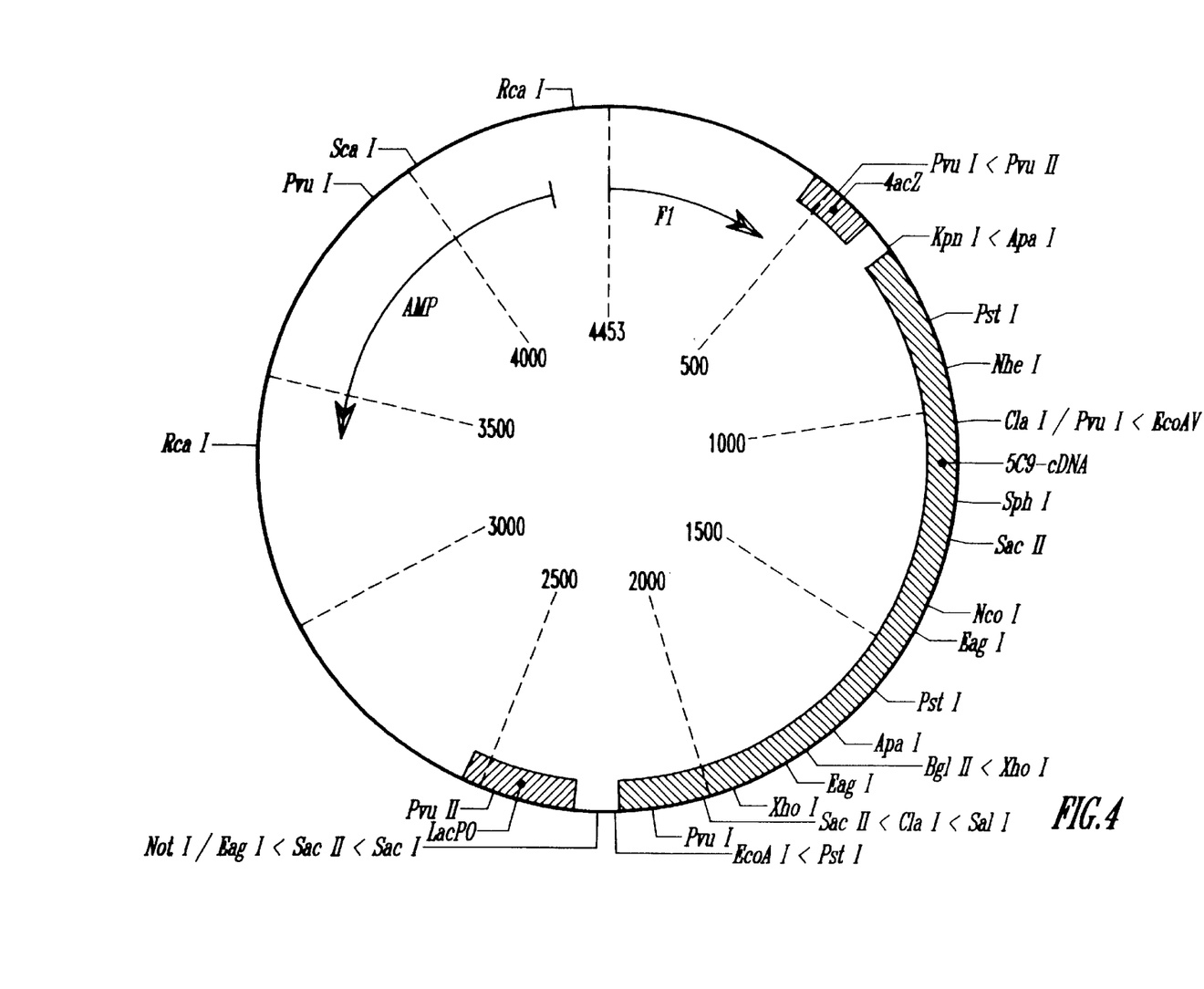
FIG. 4 is a plasmid map of the pPHP5379 plasmid, containing the 5C9 cDNA.

The present invention provides isolated maize nucleotide sequences encoding a 5C9 polypeptide, the polypeptide itself, and methods for controlling insect infestation in plants using the nucleic acids and protein of the invention.

As used herein, the term "controlling insect infestation" means reducing the number of insects that cause reduced beneficial plant yield. The reduction of insect numbers can occur either through mortality, retardation of larval development (stunting), or reduced reproductive efficiency, or a combination thereof. As used herein, the terms "insecticidal" means capable of reducing the number of insects which cause reduced beneficial yield. This reduction of insect number can, again, occur through mortality, retardation of larval development (stunting), or reduced reproductive efficiency, or a combination thereof.

As used herein, the term "nucleotide sequence" means a DNA or RNA molecule or sequence, and can include, for example, a cDNA, genomic DNA, or synthetic DNA sequence, a structural gene or a fragment thereof, or an mRNA sequence, that encodes an active or functional polypeptide.

By "transgenic plant" is meant any plant or plant cell that has become transformed by the introduction, through stable and heritable incorporation, into the subject plant or plant cell, of either native DNA that is under the control of a promoter other than the promoter that typically drives expression of that DNA in a wild-type plant, and that has been introduced back into the host plant, or foreign DNA, i.e. DNA encoding for a protein not normally found within that plant species.

"Plantlet" refers to a plant sufficiently developed to have a shoot and a root that is asexually reproduced by cell culture.

"Explant" refers to a section or piece of tissue from any part of a plant for culturing.

The term "callus" and its plural "calli", refer to an unorganized group of cells formed in response to cutting, severing, or other injury inflicted on plant tissue. Excised pieces of plant tissue and isolated cells can be induced to form callus under the appropriate culture conditions. Callus can be maintained in culture for a considerable time by transferring or subculturing parts of the callus to fresh medium at regular intervals. The transfer of callus to liquid medium leads to dispersion of the tissue and the formation of a plant cell suspension culture. Callus can be induced to undergo organized development to form shoots and roots.

"Embryoid" refers to a structure similar in appearance to a plant zygotic embryo.

"Somatic hybrid" and "somatic hybridization" refers generally to stable combination of cellular material, be it protoplast/protoplast or protoplast/cytoplast combinations, and includes cybrids and cybridization.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A polyadenylation signal and transcription termination sequence will usually be located 3' to the coding sequence.

A "promoter sequence" or a "promoter" is a DNA regulatory region capable of binding RNA polymerase in a cell and initiating transcription of a downstream (3' direction) coding sequence. For purposes of defining the present invention, the promoter sequence is bound at its 3' terminus by the translation start codon (ATG) of a coding sequence and extends upstream (5' direction) to include the minimum number of bases or elements necessary to initiate transcription. Within the promoter sequence will be found a transcription initiation site, as well as protein binding domains responsible for the binding of RNA polymerase. Eucaryotic promoters will often, but not always, contain "TATA" boxes and "CAT" boxes. Procaryotic promoters can contain Shine-Dalgarno sequences.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence is "operably linked to" or "under the control of" control sequences in a cell when RNA polymerase will bind the promoter sequence and transcribe the coding sequence into mRNA, which is then translated into the polypeptide encoded by the coding sequence.

A "host cell" is a cell which has been transformed, or is capable of undergoing transformation, by an autologous or an exogenous DNA sequence.

A cell has been "transformed" by autologous or exogenous DNA when such DNA has been introduced inside the cell membrane. The DNA may or may not be integrated into (covalently linked to) chromosomal DNA making up the genome of the transformed cell. In procaryotes and yeasts, for example, the DNA may be maintained on an episomal element, such as a plasmid. With respect to eucaryotic cells, a stably transformed cell is one in which the DNA has become integrated into the chromosome so that it is inherited by daughter cells through chromosome replication. This stability is demonstrated by the ability of the eucaryotic cell to establish cell lines or clones comprised of a population of daughter cells containing the DNA.

A "clone" is a population of cells derived from a single cell or common ancestor by mitosis. A "cell line" is a clone of a primary cell that is capable of stable growth in vitro for many generations.

Two DNA, RNA or polypeptide sequences are "substantially homologous" or "structurally equivalent" when at least about 85% (preferably at least about 90%, and most preferably at least about 95%) of the nucleotides or amino acids match over a defined length of the molecule. DNA sequences that are substantially homologous can be identified in a Southern hybridization experiment under, for example, stringent conditions, as defined for that particular system. Defining appropriate hybridization conditions is within the skill of the art. See, e.g., Maniatis et al., *Molecular Cloning, A Laboratory Manual*, Cold Spring Harbor Laboratory, New York (1982); Brown T. A., *Gene Cloning: An Introduction* (2d Ed.), Chapman & Hall, London (1990). Specifically, stringent hybridization conditions are set forth by Maniatis et al., at pages 387–389, as follows:

HYBRIDIZATION OF SOUTHERN FILTERS

1. Float the baked filter on the surface of 6×SSC until it wets from beneath. Immerse the filter in the 6×SSC for 2 minutes.

2. Slip the wet filter into a heat-sealable plastic bag (e.g. Sears' Seal-n-Save).

3. Add 0.2 ml of prehybridization fluid warmed to 68° C. for each square centimeter of nitrocellulose filter.

Prehybridization Fluid
   6×SSC
   0.5% SDS
   5×Denhardt's solution (see page 448)
   100 µg/ml denatured, salmon sperm DNA (see page 327)

4. Squeeze as much air as possible from the bag. Seal the open end of the bag with the heat sealer. Incubate the bag for 2–4 hours submerged in a water bath at 68° C.

Often, small bubbles of air form on the surface of the filter as the temperature of the prehybridization solution rises to 68° C. It is important that these bubbles be removed by occasionally agitating the fluid in the bag; otherwise the components of the prehybridization fluid will not be able to coat the filter evenly.

5. Remove the bag from the water bath. Open the bag by cutting off one corner with scissors. Squeeze out as much prehybridization solution as possible.

6. Using a pasteur pipette, add the hybridization solution to the bag. Use just enough solution to keep the filter wet (50 µl/cm² of filter).

Hybridization Solution
   6×SSC
   0.01M EDTA
   $^{32}$P-labeled denatured probe DNA
   5×Denhardt's solution
   0.5% SDS
   100 µg/ml denatured, salmon sperm DNA Typical hybridization conditions for Southern filters are given in Table 11.1.

7. Squeeze as much air as possible from the bag. Seal the cut edge with the heat sealer so that as few air bubbles as possible are trapped in the bag.

TABLE 11.1

HYBRIDIZATION CONDITIONS FOR SOUTHERN FILTERS

| DNA on Filter | Sp. Act. of probe DNA (cpm/µg) | Amount of probe added | Time of hybridization (hr) |
|---|---|---|---|
| Fragments of Cloned DNA (~100 ng/fragment) | 10$^7$ | 10$^5$–10$^6$ cpm (0.01–0.1 µg) | 3–4 |
| Total eukaryotic DNA (10 µg) | 10$^8$ | 1 × 10$^7$ cpm –5 × 10$^7$ (0.1–0.5 µg) | 12–16 |

8. Incubate the bag submerged in a water bath at 68° C. for the required hybridization period.

9. Remove the bag from the water bath and quickly cut along the length of three sides. Using gloves, remove the filter and immediately submerge it in a tray containing a solution of 2×SSC and 0.5% SDS at room temperature.

Note. Do not allow the filter to dry out at any stage during the washing procedure.

10. After 5 minutes, transfer the filter to a fresh tray containing a solution of 2×SSC and 0.1% SDS and incubate for 15 minutes at room temperature with occasional gentle agitation.

11. Transfer the filter to a flat-bottomed plastic box containing a solution of 0.1×SSC and 0.5% SDS. Incubate at 68° C. for 2 hours with gentle agitation. Change the buffer and continue incubating for a further 30 minutes.

Note. If the homology between the probe and the DNA bound to the filter is inexact, the washing should be carried out under less stringent conditions. In general, washing should be carried out at $T_m$–12° C.

The following relationships are useful:

a. $T_m$=69.3+0.41·(G+C)%–650/L.

L equals the average length of the probe in nucleotides (Marmur and Doty 1962; Wetmer and Davidson 1968).

b. The $T_m$ of a duplex DNA decreases by 1° C. with every increase of 1% in the number of mismatched base pairs (Bonner et al. 1973).

c. $(T_m)\mu_2 - (T_m)\mu_1 = 18.5 \log_{10} \frac{\mu_2}{\mu_1}$ where $\mu_1$ and $\mu_2$ are the ionic strengths of two solutions (Dove and Davidson 1962).

12. Dry the filter at room temperature on a sheet of Whatman 3MM paper.

13. Wrap the filter in Saran Wrap and apply to X-ray film to obtain an autoradiographic image (see page 470).

Notes

Hybridization may also be carried out in:

a. flat-bottomed plastic boxes.

b. buffers containing formamide. Each increase of 1% in the formamide concentration lowers the $T_m$ of a DNA duplex by 0.7° C. (McConaughy et al. 1969; Casey and Davidson 1977).

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacterium. Another example of a heterologous coding sequence is a construct where the coding sequence itself is not found in nature (e.g., synthetic sequences having codons different from the native gene). "Heterologous" DNA also refers to DNA not found within the host cell in nature. Allelic variation or naturally occurring mutational events do not give rise to a heterologous region of DNA, as these terms are used herein. "Native", "autologous" or "endogenous" DNA, as used herein, refer to DNA that is typically present in the host in nature.

The term "polypeptide" as used herein is used in its broadest sense, i.e., any polymer of amino acids (dipeptide or greater) linked through peptide bonds. Thus, the term "polypeptide" includes proteins, oligopeptides, protein fragments, analogues, fusion proteins and the like. The term also encompasses amino acid polymers as described above that include additional non-amino acid moieties. Thus, the term "polypeptide" includes glycoproteins, lipoproteins, phosphoproteins, metalloproteins, nucleoproteins, as well as other conjugated proteins. The term "polypeptide" contemplates polypeptides as defined above that are recombinantly produced, isolated from an appropriate source, or synthesized.

Insecticidally effective amounts of the 5C9 polypeptide can be effectively applied to infested plants by spray, dust or other formulation common in the art. This can be achieved by spraying or dusting with appropriate compositions comprising insecticidally effective amounts of the 5C9 protein in an appropriate carrier, as necessary, taking into account the environmental conditions at and around the time of application, the location and extent of insect infestation, and the like. The 5C9 protein for such application can be produced in bacterial or plant bioreactors capable of expressing large amounts of active protein that can be purified to the extent necessary and prepared for such application.

Alternatively, the peptide can be incorporated into the tissues of a susceptible plant so that in the course of infesting the plant the insects will be exposed to insecticidally effective amounts of the peptide. Known methods of doing this are to incorporate the peptide in a non-phytotoxic carrier which is adapted for systemic administration to the susceptible plants, such as an endophytic bacterium or a lipid vesicle or microsphere.

See, for example, U.S. Pat. No. 5,157,207, issued Oct. 20, 1992 to Carlson, et al., the disclosures of which are hereby incorporated by reference, directed to modified plants containing bacterial inoculants. According to the '207 patent, certain types of microorganisms, such as hybrid agricultural-chemical-producing endosymbiotic microorganisms, can colonize the interior of plants and provide useful agricultural chemicals, such as pesticides, to the plants. Certain microbial endophytes are capable of inducing enhanced resistance in a host to phytopathogens. The bacteria that are suitable for use in such a method in this invention belong to a species of bacteria that is capable of replicating in the interior tissues of a plant and of producing the desired compound of this invention. Under normal field conditions, the bacterium does not ordinarily inhabit the seed or the plant into which the bacterium is introduced. Such a bacterium can be a gram-positive bacterium, a gram-negative bacterium or a species of actinomycetes. The bacterium is modified by genetic engineering techniques to incorporate the gene coding for the compound of this invention. In a preferred embodiment, the bacterial cell is a genetically modified species of either Corynebacteria, Clavibacter, Pseudomonas, Xanthomonas or Erwinia, the Corynebacteria and clavibacters being as defined in Davis M. J. et al. (1984), loc. cit. In a particularly preferred embodiment, the bacterial cell is a strain of *Clavibacter xyli*. In a most preferred embodiment, the bacterial cell is a *Clavibacter xyli* subspecies *cynodontis*.

Reference also may be had to U.S. Pat. No. 5,252,348, issued Oct. 12, 1993 and directed to "Artificial viral envelopes", the disclosures of which are also hereby incorporated herein by reference. According to the '348 patent, lipid vesicles of the patent can be used to transfer biological material to plant cells.

Further reference may be had to U.S. Pat. No. 5,071,654, issued Dec. 10, 1991, the disclosures of which are hereby incorporated by reference and which are directed to insecticidal compositions involving a phospholipid vesicle with insect midgut brush border and a *Bacillus thuringiensis* protein endotoxin incorporated therein and an agriculturally-acceptable carrier. Such phospholipid vesicle compositions are stated to provide a vehicle for the application of delta endotoxin to plants. The vesicles are stated to act in much the same fashion as liposomes do in vertebrates, to facilitate the delivery of the toxins to the target midgut cells in susceptible insects.

Reference may also be had to U.S. Pat. No. 5,034,322, issued Jul. 23, 1991 to Rogers, et. al., the disclosures of which are hereby incorporated by reference and which are directed to chimeric genes suitable for expression in plant cells, but which discusses methods capable of inserting the chimeric genes of this invention into plant cells, although the reported transformation efficiencies achieved to date by such methods have been low. Discussed methods include use of lipid vesicles, also called liposomes, from which DNA may be taken up by plant cells.

Still further reference may be had to U.S. Pat. No. 4,588,578, issued May 13, 1986 to Fountain, et. al. and directed to monophasic vesicles for delivery of antimicrobials and other compounds to plants, and U.S. Pat. No. 4,522,803, issued Jun. 11, 1985 to Lenk, et. al. and directed, inter alia, to methods for treatment of infections in plants, comprising administering stable plurilamellar vesicles containing a compound effective for treating said infection. The disclosures of these patents are also hereby incorporated by reference.

The foregoing and similar methods are commonly employed with insecticidal materials which are designed to attack chewing insects and are well within the purview of one of ordinary skill in the art of insecticide and larvicide formulation and are fully contemplated in the practice of this invention. However, genes which code for the peptides of this invention can be readily synthesized using automated methods, cloned, inserted into an appropriate expression cassette, and introduced directly into cells of a susceptible plant species. Accordingly, an especially preferred embodiment of this method involves inserting into the genome of the plant a DNA sequence coding for the polypeptide of this invention in proper reading frame, together with transcription initiator and promoter sequences active in the plant. Transcription and translation of the DNA sequence(s) under control of the regulatory sequences can cause expression of the polypeptide sequence(s) at levels which provide an insecticidally effective amount of the polypeptide(s) in the tissues of the plant which are normally infected by the pests.

With a working knowledge of conventional techniques for cloning, DNA isolation, amplification and purification, for enzymatic reactions involving DNA ligase, DNA polymerase, restriction endonucleases and the like, and various separation techniques known and commonly employed by those skilled in the art (See, for example, R. Wu, ed. (1979) *Meth. Enzymol.* 68; R. Wu et al., eds. (1983) *Meth. Enzymol.* 100, 101: L. Grossman and K. Moldave, eds. (1980) *Meth. Enzymol.* 65: J. H. Miller (1972) Experiments in Molecular Genetics; R. Davis et al. (1980) *Advanced Bacterial Genetics*; R. F. Schleif and P. C. Wensink (1982) *Practical Methods in Molecular Biology*; and T. Manniatis et al. (1982) *Molecular Cloning.*), one of ordinary skill can employ any suitable gene construct containing the structural genes coding for the peptides of this invention.

The nucleotide sequence which when expressed imparts insecticidal activity is a structural gene which codes for the polypeptide of this invention, or its structural and functional equivalents. Given the amino acid sequence provided herein, any of several translationally equivalent synthetic DNA sequences can then be prepared which code for the sequence of amino acids using commercially available software, such as PC Gene™ or GCG™, and this synthetic sequence can be inserted into an appropriate plant expression cassette.

In carrying out this invention, it will be appreciated that numerous plant expression cassettes and vectors are well known in the art. By the term "expression cassette" is meant a complete set of control sequences including initiation, promoter and termination sequences which function in a plant cell when they flank a structural gene in the proper reading frame. Expression cassettes frequently and preferably contain an assortment of restriction sites suitable for cleavage and insertion of any desired structural gene. It is important that the cloned gene have a start codon in the correct reading frame for the structural sequence. In addition, the plant expression cassette preferably includes a strong promoter sequence at one end to causes the gene to be transcribed at a higher frequency, and a poly-A recognition sequence at the other end for proper processing and transport of the messenger RNA. An example of a preferred (empty) expression cassette into which the DNA sequence of the present invention can be inserted is the pPHI414 plasmid developed by Beach et al. of Pioneer Hi-Bred International, Inc., Johnston, Iowa. Preferred plant expression cassettes can be designed to include one or more selectable marker genes, including, for example, kanamycin resistance or herbicide tolerance genes.

By the term "vector" herein is meant a DNA sequence which is able to replicate and express a foreign gene in a host cell. Typically, the vector has one or more endonuclease recognition sites which may be cut in a predictable fashion by use of the appropriate enzyme. Such vectors are preferably constructed to include additional structural gene sequences imparting antibiotic or herbicide resistance, which then serve as selectable markers to identify and separate transformed cells. Preferred selection agents include, for example, kanamycin, chlorosulfuron, phosphonothricin, hygromycin and methotrexate, and preferred markers are genes conferring resistance to these compounds. A cell in which the foreign genetic material in a vector is functionally expressed has been "transformed" by the vector and is referred to as a "transformant". A "foreign" gene refers to any gene introduced into a plant by transformation techniques, and can include autologous genes re-introduced into the plant species from which the gene or nucleotide sequence was isolated. Typically such autologous genes will have been put under the control of a promoter different from the promoter that is operably linked to the autologous gene in a wild type plant.

A particularly preferred vector is a plasmid, by which is meant a circular double-stranded DNA molecule that is not a part of the chromosomes of the cell.

As mentioned above, genomic, synthetic and cDNA representing the 5C9 gene and encoding the 5C9 polypeptide may be used in this invention. The vector of interest may also be constructed partially from a cDNA clone, partially from a synthetic sequence and/or partially from a genomic clone. When the 5C9 gene sequence is in hand, genetic constructs are made which contain the necessary regulatory sequences to provide for efficient expression of the gene in the host cell. According to this invention, the genetic construct will contain a genetic sequence coding for the 5C9 polypeptide and one or more regulatory sequences operably linked on either side of the nucleotide sequence encoding the 5C9 polypeptide. Typically, the regulatory sequences will be selected from the group comprising of promoters and terminators. The regulatory sequences may be from autologous or heterologous sources.

Promoters that may be used in the genetic sequence include, for example, nos, ocs, phaseolin, caMV, FMV, ubiquitin and other promoters isolated from the DNA of plants or other sources, both natural and synthetic. A tissue-specific promoter can be used in instances where it may be desirable to localize production of the 5C9 expression product to a particular tissue type.

An efficient plant promoter that may be used is an overproducing plant promoter. Overproducing plant promoters that may be used in this invention include the promoter of the small sub-unit (ss) of the ribulose-1, 5-bisphosphate carboxylase from soybean (Berry-Lowe et al., *J. Molecular and App. Gen.*, 1:483–498 (1982)), and the promoter of the chlorophyll a-b binding protein. These two promoters are known to be light-included in eukaryotic plant cells (see, for example, *Genetic Engineering of Plants, An Agricultural Perspective*, Cashmore, Pelham, N.Y., 1983, pp. 29–38, G. Coruzzi et al., *J. Biol. Chem.*, 258:1399 (1983), and P. Dunsmuir, et al., *J. Molecular and App. Gen.*, 2:285 (1983)) and may be particularly desirable in the practice of the present invention. An especially preferred constitutive promoter is the 35S promoter from Cauliflower Mosaic Virus.

Root-specific promoters are also known and can be selected from the many available from the literature or isolated de novo from various compatible species. For example, Hirel, B., Marsolier, M. C., Hoarau, A., Hoarau, J., Brangeon, J., Schafer, R., and Verma, D. P. S., *Plant Molecular Biology*, October 1992. v. 20 (2), pp. 207–218, describe a root-specific glutamine synthetase gene from soybean. Keller, B. and Baumgartner, C., *The Plant Cell*, October 1991, v. 3 (10), pp. 1051–1061, describe a root-specific control element in the GRP 1.8 gene of French bean. Sanger, M., Daubert, S., and Goodman, R. M., *Plant Molecular Biology*, March 1990, v. 14 (3), pp. 433–443, discuss the root-specific promoter of the Mannopine Synthase (MAS) gene of *Agrobacterium tumefaciens*. Miao, G. H., Hirel, B., Marsolier, M. C., Ridge, R. W., and Verma, D. P. S., *The Plant Cell*, January 1991, v. 3 (1), pp. 11–22, describe a full-length cDNA clone encoding cytosolic glutamine synthetase (GS), which is expressed in roots and root nodules of soybean. Bogusz, D., Llewellyn, D. J., Craig, S., Dennis, E. S., Appleby, C. A., and Peacock, W. J., *The Plant Cell*, July 1990, v. 2(7), pp. 633–641, discusses two root-specific promoters isolated from hemoglobin genes from the nitrogen-fixing nonlegume *Parasponia andersonii* and the related non-nitrogen-fixing nonlegume *Trema tomentosa*. The promoters of these genes were linked to a beta-glucuronidase reporter gene and introduced into both the nonlegume *Nicotiana tabacum* and the legume *Lotus corniculatus*, and in both instances root-specific promoter activity was preserved. Leach, F. and Aoyagi, K., *Plant Science* (Limerick) 1991, 79 (1):69–76, describe their analysis of the promoters of the highly expressed ro1C and ro1D root-inducing genes of *Agrobacterium rhizogenes*. They concluded that enhancer and tissue-specific DNA determinants are dissociated in those promoters. Teeri, T. H., Lehvaslaiho, H., Franck, M., Uotila, J., Heino, P., Palva, E. T., Montagu, M. van, and Herrera-Estrella, L., *EMBO Journal*, 1989, 8 (2):343–350, used gene fusions to lacZ to show that the Agrobacterium T-DNA gene encoding octopine synthase is especially active in the epidermis of the root tip and that the TR2' gene was root specific in the instant plant and stimulated by wounding in leaf tissue, an especially desirable combination of characteristics for use with an insecticidal or larvicidal gene. The TR1' gene, fused to NPTII, (neomycin phosphotransferase II) showed similar characteristics.

Various promoters particularly useful in plants are disclosed and discussed in U.S. Pat. No. 5,234,834 (Fischer et al., Aug. 10, 1993). Fischer et al. also discuss expression cassette and vector construction useful for plant genetic applications.

The expression cassette comprising the nucleotide sequence coding for the 5C9 polypeptide operably linked to the desired control sequences can be ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotyic selection markers in transformed host cells. Typically, genes conferring resistance to antibiotics or selected herbicides are used. After the genetic material is introduced into the target cells, successfully transformed cells and/or colonies of cells can be isolated by selection on the basis of these markers.

Typically, an intermediate host cell will be used in the practice of this invention to increase the copy number of the cloning vector. With an increased copy number, the vector containing the gene of interest can be isolated in significant quantities for introduction into the desired plant cells. Host cells that can be used in the practice of this invention include prokaryotes, including bacterial hosts such as *E. coli, S. typhimurium*, and *S. marcescens*. Eukaryotic hosts such as yeast or filamentous fungi may also be used in this invention.

The isolated cloning vector will then be introduced into the plant cell using any convenient technique, including, for example, chemically induced uptake, electroporation, liposomes, retroviruses, electrophoresis, microparticle bombardment, and microinjection into cells from any plant species, including monocotyledonous or dicotyledonous plants, in cell or tissue culture or in whole plants where applicable, to provide transformed plant cells or plants containing as foreign DNA at least one copy of the DNA sequence of the plant expression cassette. Using known techniques, protoplasts can be regenerated and cell or tissue culture can be regenerated to form whole fertile plants which carry and express the desired gene for the selected protein. See generally Chapters 6, 7 and 9 in Glick and Thompson, *Methods in Plant Molecular Biology and Biotechnology*, CRC Press, Boca Raton, 1993.

It will also be appreciated by those of ordinary skill that the plant vectors provided herein can be incorporated into *Agrobacterium tumefaciens*, which can then be used to transfer the vector into susceptible plant cells. Thus, this invention provides a method for insect control in *Agrobacterium tumefaciens*-susceptible plants in which the expression cassette is introduced into the cells by infecting the cells with *Agrobacterium tumefaciens*, a plasmid of which has been modified to include a plant expression cassette which expresses 5C9 in the manner of this invention.

The invention envisions transformation of both monocotyledonous and dicotyledonous species of plants. Preferred monocot species include, for example, maize, sorghum, wheat, and rice. Preferred dicots include, for example, soybeans, sunflowers, rapeseed (for example, canola), and peanuts. These monocots and dicots can be transformed using microprojectile bombardment methods that have been widely published. Other monocot species, such as Asparagus, and many of the dicot species listed above, as well as sunflower, alfalfa, tobacco, cotton and tomato can be transformed using an Agrobacterium species such as *Agrobacterium rhizogenes* or *Agrobacterium tumefaciens.*

This invention also provides methods of imparting resistance to insects to plants of a susceptible taxon comprising culturing regenerable cells or tissues from at least one plant from the taxon, introducing into the cells of the cell or tissue culture at least one copy of an expression cassette comprising a gene which codes for the polypeptide of this invention, operably linked to plant regulatory sequences which cause the expression of peptide(s) in the cells, and regenerating insect resistant whole plants from the cell or tissue culture. Once whole plants have been obtained, they can be sexually or clonally reproduced in such manner that at least one copy of the sequence provided by the expression cassette is present in the cells of progeny of the reproduction.

Alternatively, once a single transformed plant has been obtained by the foregoing recombinant DNA method, conventional plant breeding methods can be used to transfer the structural gene for the 5C9 polypeptide and associated regulatory sequences via crossing and backcrossing. Such intermediate methods will further comprise sexually crossing the insect-resistant plant with a plant from the infestation-susceptible taxon, recovering reproductive material from the progeny of the cross, and growing insect-resistant plants from the reproductive material. Where desirable or necessary, the agronomic characteristics of the susceptible taxon can be substantially preserved by expanding this method to include the further steps of repetitively backcrossing the insect-resistant progeny with infestation-susceptible plants from the susceptible taxon, and selecting for expression of insecticidal activity (or an associated marker gene) among the progeny of the backcross, until the desired percentage of the characteristics of the susceptible taxon are present in the progeny along with the gene imparting insecticidal activity.

The following description further exemplifies the compositions of this invention and the methods of making and using them. However, it will be understood that other methods, known by those of ordinary skill in the art to be equivalent, can also be employed.

EXAMPLE 1

Generation of 5C9 cDNA

A subtracted maize tassel cDNA library was constructed for the isolation of tissue specific genes. Weiss et al., Isolation of cDNAs Encoding Guanine Nucleotide-binding Protein β-submit Homologues From Maize (ZGB1) and Arabidopsis (AGB1), P.N.A.S. 91:9554–9558, 1994. Individual clones were transferred to microtiter plates, in glycerol stocks. Clones were selected at random and used to probe Northern blots using Enhanced Chemiluminescence (ECL) system from Amersham. An ECL labeled probe of approximately 0.6 kb hybridized only with approximately 1.9 kb mRNA from tassels at different developmental stages.

A second tassel cDNA library was screened with the approximately 0.6 kb probe and two more cDNA clones were isolated. Restriction digest analysis indicated that plasmid pPHP5379 contains nearly full length coding sequence for 5C9.

A maize genomic library constructed from inbred line A632, was probed with inserts from pPHP5379, and two overlapping clones, 5C9.5 and 5C9.10, were isolated and purified. Restriction digest analysis and subcloning of genomic fragments from 5C9.5 were performed, in pPHP5827 and pPHP5828, with XbaI genomic fragment into pSKII plus in both orientations, and pPHP5530, Bam HI/NotI genomic fragment into pKSII plus.

Another Northern membrane was probed with $^{32}P$ labeled 5C9. After 24 hours exposure, high levels of hybridization signal was visible with mRNA from premeiotic stage tassels, as well as from 7 day post-pollinated kernels, and lesser signal was detected with meiotic stage tassels, quartet stage tassels and uninucleate stage tassels. The hybridization signal was barely detectable with mRNA from binucleate stage tassels, 21 day post-pollinated kernels, 14 day post-pollinated kernels, and from 12 cm long ear shoot. After 90 hours exposure, signal was faintly detectable with mRNA from 6 day seedling green leaves, 6 day old seedling roots, and from ear shoots.

EXAMPLE 2

Protein Expression in Plants

Transgenic plants can be produced using any of several art-recognized methods. See, generally, Glick and Thompson, *Methods in Plant Molecular Biology and Biotechnology*, CRC Press, Boca Raton, 1993. For example, microprojectile bombardment can be utilized to transform maize callus, and whole, stably transformed plants regenerated therefrom. Such plants are transformed with a cDNA or genomic DNA or synthetic DNA sequence coding for the 5C9 polypeptide or a structural equivalent, operably linked to an over-producing promoter that drives expression of the polypeptide, either constitutively or in a tissue specific manner. Such plants are then tested for resistance to insect infestation using art-recognized techniques.

A plant expression cassette, employing the regulatory sequences developed by Beach, et al., and containing the 5C9 protein gene, is constructed. This plasmid contains an enhanced 35S promoter spanning nucleotides −421 to +2 of Cauliflower Mosaic Virus with the region from −421 to −90 duplicated in tandem, a 79 bp HindIII SaI1 fragment from pJII101 spanning the 5' leader sequence of Tobacco Mosaic Virus, a 579 bp fragment spanning the first intron from maize AdH1-S, and a 281 bp fragment spanning the polyadenylation site from the nopaline synthase gene in pTiT37. Alternative promoters, for example the ubiquitin promoter or the wheat Ta peroxidase promoter, and including tissue specific promoters, can also be utilized.

Another construct that can be used as an expression cassette differs from pPHI414 in that it lacks the AdH intron segment. However, like pPHI414, it is constructed to have numerous restriction sites between the O' segment and the NOS segment, which sites can be conveniently used for splicing any desired protein structural gene into position.

The vector can be cotransformed with a similar plasmid containing a selectable marker, for example a marker for antibiotic or herbicide resistance, into Black Mexican Sweet corn protoplasts using art recognized transformation methods, for example electroporation or microprojectile bombardment. These protoplasts can then be induced to regenerate cell walls and develop into callus by conventional techniques. Likewise, this callus can then be subjected to selection to select for transformed colonies, and these colonies can be tested for expression of protein with antisera for the appropriate protein using known methods. The efficiency of protection can be measured by infesting callus (or suspension cultures derived from callus) with the target insect and measuring survival percentages.

The protein gene can be introduced into embryogenic maize callus and other tissues by methods similar to those used for Black Mexican Sweet. A particularly preferred transformation method is microprojectile bombardment. Embryogenic callus of numerous elite lines has been regenerated to produce whole fertile plants. When normal integration of the transgene occurs, the insect resistance imparted by the endogenous production of the protein can be expected to be simply inherited, dominant trait and can therefore be introduced into other plant varieties of the species by simple crossing or backcrossing if desired.

Using the foregoing techniques, the gene that codes for the 5C9 protein of this invention can be introduced into maize cells, and the expression of protein in such cells can be determined by transient assays.

All publications and patents mentioned in this specification are hereby incorporated herein by reference.

What is claimed is:

1. An isolated polypeptide encoded by the polynucleotide of SEQ ID NO: 1or by a polynucleotide that hybridizes with the polynucleotide of SEQ ID NO: 1 under stringent conditions.

2. An isolated polypeptide having the amino acid sequence shown in SEQ ID NO: 2.

3. An insecticidally effective composition for application to plants comprising an insecticidally effective amount of the 5C9 polypeptide having the amino acid sequence of SEQ ID NO: 2 in a non-phytotoxic carrier.

4. The composition of claim 2 wherein the carrier is adapted for systemic administration to a plant.

5. The composition of claim 2 wherein the carrier is adapted for topical administration to a plant.

6. A method of controlling insect infestation of a plant comprising providing an insecticidally effecting amount of the polypeptide of claim 1 for ingestion by the insect.

7. The method of claim 5 wherein the polypeptide is provided by delivery of the composition comprising a non-phytotoxic carrier thereof into the environment of the plant.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1531 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

```
GAATTCGGCA  CGAGCACACA  CAAGCGAGGA  GCACTACCTG  TTGGTTGGAT  TCTCTTCAGT      60

CTAGCTACTC  GATCGGTCCC  TTGTCCACAG  TTAAGTTTCA  GACACATGGG  GAGCATTGGC     120

AGAGGCACGG  CCAACTGCGC  CACCGTGCCG  CAGCCGCCGC  CGTCGACAGG  GAAGCTCATC     180

ACGATCCTGA  GCATCGATGG  CGGCGGCATC  CGCGGCCTTA  TCCCGGCGAC  CATCATTGCG     240

TACCTCGAGG  CCAAGCTCCA  GGAGCTGGAC  GGCCCGGACG  CTCGGATCGC  CGACTACTTC     300

GATGTGATTG  CCGGGACGAG  CACCGGCGCC  CTGCTCGCGT  CGATGCTGGC  GGCGCCGGAC     360
```

```
GAGAACAACC  GGCCGCTGTT  CGCCGCCAAG  GACCTCACCA  CGTTCTACCT  CGAGAACGGC      420

CCAAAGATCT  TCCCACAGAA  AAAGGCTGGG  TTGCTGACGC  CGCTGAGGAA  CCTGCTGGGC      480

CTGGTGCGGG  GCCCCAAGTA  CGACGGCGTG  TTCCTGCACG  ACAAGATCAA  GAGCCTGACG      540

CACGACGTCA  GGGTGGCGGA  CACGGTGACC  AACGTCATCG  TGCCGGCGTT  CGACGTCAAG      600

TACCTGCAGC  CCATCATCTT  CTCGACGTAC  GAGGCCAAGA  CCGACACCCT  CAAGAACGCG      660

CACCTCTCCG  ACATCTGCAT  CAGCACGTCG  GCGGCGCCCA  CCTACTTCCC  GGCGCACTTC      720

TTCAAGACCG  AGGCCACCGA  CGGCCGGCCC  CCCCGCGAGT  ACCACCTCGT  GGACGGCGGC      780

GTCGCGGCCA  ACAACCCCAC  CATGGTCGCC  ATGTCCATGC  TCACCAAGGA  GGTGCACCGC      840

CGCAACCCCA  ACTTCAACGC  CGGCAGCCCC  ACCGAGTACA  CCAACTACCT  CATCATCTCC      900

GTCGGCACCG  GGTCGGCAAA  GCAGGCGGAG  AAGTACACCG  CGGAGCAGTG  CGCGAAGTGG      960

GGCCTCATCC  AGTGGCTCTA  CAACGGCGGC  TTCACGCCGA  TCATCGACAT  CTTCTCGCAT     1020

GCCAGTTCCG  ACATGGTTGA  CATCCATGCG  TCGATCCTCT  TTCAGGCCCT  GCACTGCGAG     1080

AAGAAGTACC  TTCGCATCCA  GGATGATACT  TTGACTGGGA  ACGCATCGTC  CGTGGACATC     1140

GCCACCAAGG  AGAACATGGA  GTCTCTGATA  TCGATCGGCC  AGGAGCTGCT  CAAGAAGCCA     1200

GTGGCGAGAG  TGAACATCGA  CACAGGGGTG  TACGAGTCCT  GCGACGGTGA  GGGCACAAAT     1260

GCACAGTCGC  TAGCTGACTT  CGCCAAGCAA  CTCTCTGACG  AGCGCAAGCT  ACGCAAGAGC     1320

AATCTCAACT  CCAACTAATA  AATACCTCTC  TCAGTCACAG  CATGTGCTCT  TTCTGCAGAT     1380

TCACCGTTTC  TTATTTTTAA  TTTCAATTTC  AATTCAGTGT  ATGTGCGTGT  GTGTGTGACT     1440

GTACTGTGTG  TACCAATAAA  CATTTAAGTT  CAATCATTTG  CTTGTCTATG  ATCAAAAGAA     1500

CCATTTCCTT  CTGAAAAAAA  AACGGCACGA  G                                     1531
```

(2) INFORMATION FOR SEQ ID NO:2:

(i) SEQUENCE CHARACTERISTICS:
        (A) LENGTH: 410 amino acids
        (B) TYPE: amino acid
        (C) STRANDEDNESS: single
        (D) TOPOLOGY: linear     (ii) MOLECULE TYPE: protein     (xi) SEQUENCE DESCRIPTION: SEQ ID NO:2:

```
Met  Gly  Ser  Ile  Gly  Arg  Gly  Thr  Ala  Asn  Cys  Ala  Thr  Val  Pro  Gln
  1                   5                  10                  15

Pro  Pro  Pro  Ser  Thr  Gly  Lys  Leu  Ile  Thr  Ile  Leu  Ser  Ile  Asp  Gly
                 20                  25                  30

Gly  Gly  Ile  Arg  Gly  Leu  Ile  Pro  Ala  Thr  Ile  Ile  Ala  Tyr  Leu  Glu
             35                  40                  45

Ala  Lys  Leu  Gln  Glu  Leu  Asp  Gly  Pro  Asp  Ala  Arg  Ile  Ala  Asp  Tyr
     50                  55                  60

Phe  Asp  Val  Ile  Ala  Gly  Thr  Ser  Thr  Gly  Ala  Leu  Leu  Ala  Ser  Met
 65                  70                  75                  80

Leu  Ala  Ala  Pro  Asp  Glu  Asn  Asn  Arg  Pro  Leu  Phe  Ala  Ala  Lys  Asp
                 85                  90                  95

Leu  Thr  Thr  Phe  Tyr  Leu  Glu  Asn  Gly  Pro  Lys  Ile  Phe  Pro  Gln  Lys
                100                 105                 110

Lys  Ala  Gly  Leu  Leu  Thr  Pro  Leu  Arg  Asn  Leu  Leu  Gly  Leu  Val  Arg
            115                 120                 125

Gly  Pro  Lys  Tyr  Asp  Gly  Val  Phe  Leu  His  Asp  Lys  Ile  Lys  Ser  Leu
        130                 135                 140
```

-continued

```
Thr His Asp Val Arg Val Ala Asp Thr Val Thr Asn Val Ile Val Pro
145                 150                 155                 160

Ala Phe Asp Val Lys Tyr Leu Gln Pro Ile Ile Phe Ser Thr Tyr Glu
                165                 170                 175

Ala Lys Thr Asp Thr Leu Lys Asn Ala His Leu Ser Asp Ile Cys Ile
            180                 185                 190

Ser Thr Ser Ala Ala Pro Thr Tyr Phe Pro Ala His Phe Phe Lys Thr
        195                 200                 205

Glu Ala Thr Asp Gly Arg Pro Pro Arg Glu Tyr His Leu Val Asp Gly
    210                 215                 220

Gly Val Ala Ala Asn Asn Pro Thr Met Val Ala Met Ser Met Leu Thr
225                 230                 235                 240

Lys Glu Val His Arg Arg Asn Pro Asn Phe Asn Ala Gly Ser Pro Thr
                245                 250                 255

Glu Tyr Thr Asn Tyr Leu Ile Ile Ser Val Gly Thr Gly Ser Ala Lys
            260                 265                 270

Gln Ala Glu Lys Tyr Thr Ala Glu Gln Cys Ala Lys Trp Gly Leu Ile
        275                 280                 285

Gln Trp Leu Tyr Asn Gly Gly Phe Thr Pro Ile Ile Asp Ile Phe Ser
    290                 295                 300

His Ala Ser Ser Asp Met Val Asp Ile His Ala Ser Ile Leu Phe Gln
305                 310                 315                 320

Ala Leu His Cys Glu Lys Lys Tyr Leu Arg Ile Gln Asp Asp Thr Leu
                325                 330                 335

Thr Gly Asn Ala Ser Ser Val Asp Ile Ala Thr Lys Glu Asn Met Glu
            340                 345                 350

Ser Leu Ile Ser Ile Gly Gln Glu Leu Leu Lys Lys Pro Val Ala Arg
        355                 360                 365

Val Asn Ile Asp Thr Gly Val Tyr Glu Ser Cys Asp Gly Glu Gly Thr
    370                 375                 380

Asn Ala Gln Ser Leu Ala Asp Phe Ala Lys Gln Leu Ser Asp Glu Arg
385                 390                 395                 400

Lys Leu Arg Lys Ser Asn Leu Asn Ser Asn
                405                 410
```